US00PP18661P2

(12) United States Plant Patent
Austin

(10) Patent No.: US PP18,661 P2
(45) Date of Patent: Mar. 25, 2008

(54) APPLE TREE NAMED 'CANDY'

(50) Latin Name: *Malus domestica*
Varietal Denomination: Candy

(76) Inventor: David Austin, Rd 1, Upper Moutere (NZ)

( * ) Notice: Subject to any disclaimer, the term of this patent is extended or adjusted under 35 U.S.C. 154(b) by 0 days.

(21) Appl. No.: 11/400,782

(22) Filed: Apr. 6, 2006

(51) Int. Cl.
*A01H 5/00* (2006.01)

(52) U.S. Cl. ..... Plt./168

(58) Field of Classification Search ..... Plt./161, Plt./168
See application file for complete search history.

*Primary Examiner*—Kent Bell
*Assistant Examiner*—S. B. McCormick-Ewoldt
(74) *Attorney, Agent, or Firm*—Stratton Ballew PLLC

(57) ABSTRACT

A new and distinct apple tree is disclosed. 'Candy,' a limb sport of 'Aztec,' is notable for its distinctive fruit, which exhibits a 95%–100% intense red coloration, with striping present.

1 Drawing Sheet

Figure 1:
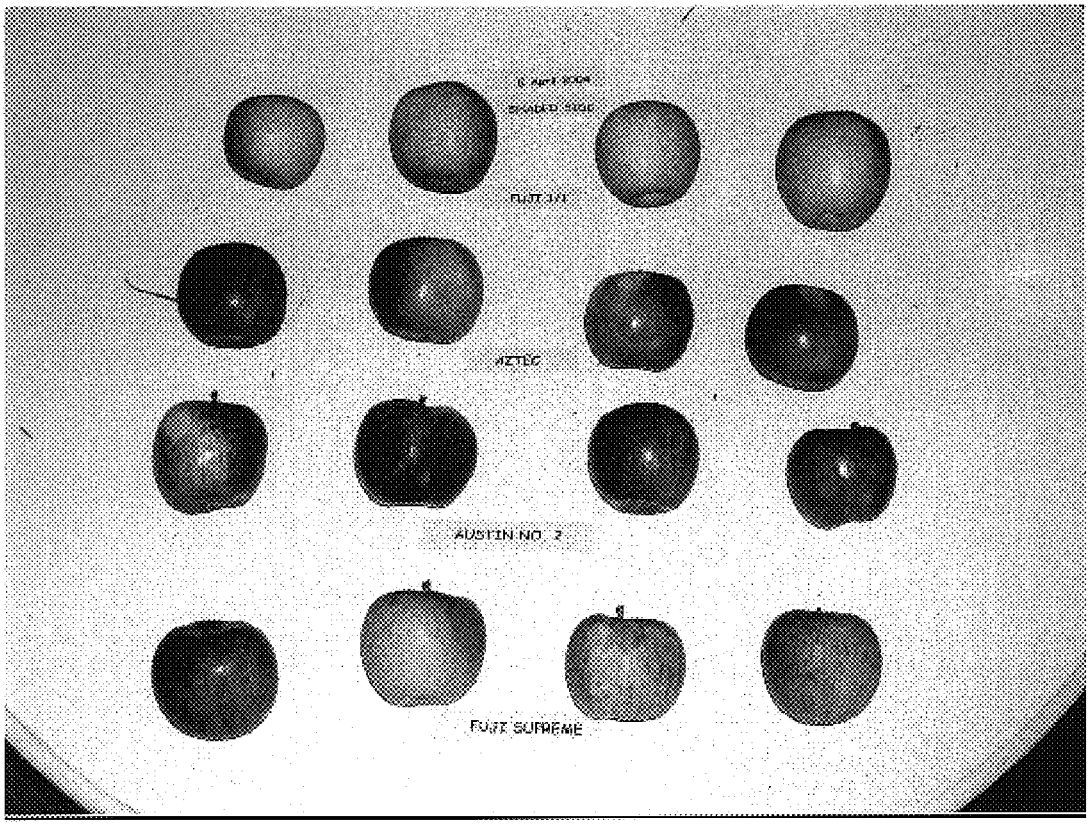

Latin name of the genus and species of the plant claimed: *Malus domestica.*
Variety denomination: 'CANDY'.

BRIEF DESCRIPTION OF THE PHOTOGRAPHS

FIG. 1 is a photograph of fruit of the claimed plant, denoted "Austin No. 2," shown with fruit of other apple varieties for comparison.

BRIEF DESCRIPTION OF THE VARIETY

The new cultivar 'Candy' originated as a limb sport mutation of 'Aztec' Fuji (not patented). It was discovered by the inventor in a cultivated orchard at Upper Moutere, Nelson, New Zealand. 'Candy' was asexually propagated by grafting at Upper Moutere, Nelson, New Zealand, and has been shown to remain true to type over successive generations.

'Candy' is distinguishable from its parent and from other known Fuji-type varieties by its distinctive coloration, as noted in Table 1 below:

TABLE 1

| Variety | Coloration |
|---|---|
| 'Candy' | 95%-100% solid red flush with fine red on green stripe over 60%-70% of fruit on unexposed side. Fine red stripe over blush red background on exposed side |
| 'Fuji 1/1' (not patented) | Generally striped with 30%-40% red blush on exposed side |
| 'Aztec Fuji' | 95%-100% solid red flush |

DETAILED BOTANICAL DESCRIPTION OF THE VARIETY

The following detailed botanical description is based on observations made during the 2005/2006 growing season at Upper Moutere, Nelson, New Zealand of five year old trees of the variety grown on MM106 rootstock. All colors are described according to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, the new variety may vary from the stated average.

Tree:
- *Vigor.*—Medium.
- *Type.*—Ramified.
- *Habit.*—Spreading.
- *Size.*—Height 4 m, diameter 2 m.
- *Trunk.*—Diameter 20 mm at 15 cm above graft union; bark texture smooth; grey brown 199A.
- *Branches.*—Length 60 cm at 1.4 m from ground; diameter 3 cm at 60 cm from trunk; crotch angle 0 to 30° above horizontal; grey brown 199A.
- *Winter hardiness.*—Hardy in area tested.
- *Chilling requirement.*—As for 'Fuji'.

Dormant one year old shoot:
- *Pubescence.*—None.
- *Size.*—Length 40 cm; diameter 5 mm.
- *Color.*—Greyed orange 175A.
- *Internode length.*—2.5 cm.
- *Number of lenticels.*—25 to 30 per internode.

Flower:
- *Buds.*—Quantity one per spur; shape pointed; length 8.5 mm; diameter 4.1 mm; greyed 201C.
- *Flower color.*—Red purple 63D (at balloon stage).
- *Size.*—Diameter 27 mm; depth 13.5 mm; quantity 5 or 6 per cluster.
- *Petals.*—Quantity per flower 5; not touching; length 16 mm; width 10 mm; apex shape rounded; base shape square; margin smooth; upper surface red purple 69D; lower surface red purple 69B when fully open.
- *Sepals.*—Quantity per flower 6; shape pointed; length 5.0 mm; green 145A.
- *Pedicel.*—Length 14 mm; diameter 1.5 mm; greyed green 195A.
- *Stamens.*—Quantity per flower — many.
- *Filaments.*—Length 7.5 to 9 mm; green yellow 1D.
- *Anthers.*—Length 1.4 mm; width 0.5 mm; yellow 8A.
- *Pistil.*—Length 8.9 mm.

*Stigma.*—Length 0.7 mm; yellow orange 16A.
*Style.*—Length 4.9 mm; yellow green 150C.
*Ovary.*—Length 3.8 mm; yellow green 150D.
*Time of flowering.*—Very early; first bloom 30 September, full bloom 7 October (2007 growing season, National Cultivar Centre, Havelock North, New Zealand).
*Pollination.*—As for Fuji; any diploid cultivar (other than Fuji or Fuji sport) which flowers at a similar time will serve as a pollenizer for 'Candy'.

Leaf:
*Attitude in relation to shoot.*—Upward.
*Length.*—Medium, avg. 7.0 cm.
*Width.*—Medium, avg. 4.0 cm.
*Length-width ratio.*—Medium.
*Shape.*—Elliptic; tip pointed, base equilateral.
*Margin.*—Crenate.
*Color.*—Upper surface green 146B; lower surface green 147C.
*Petiole.*—Length 3.6 mm; diameter 1 mm; upper surface greyed green 197C; lower surface greyed green 195B; greyed purple 185B.
*Venation.*—As for Fuji; greyed green 195B.
*Pubescence.*—Leaf lower surface and petiole mildly pubescent.

Fruit:
*Size.*—Medium to Large, diameter 6.8 cm, height 7.5 cm, about 200 g.
*General shape in profile.*—Globose.
*Position of maximum diameter.*—Middle of fruit.
*Ribbing.*—Not present.
*Aperture of eye.*—Closed.
*Size of eye.*—Diameter 3 mm.
*Size of eye basin.*—Depth 1.6 cm; width 3.8 cm.
*Stalk.*—Diameter 3.5 mm; length 1 cm; red 45A at tip fading to greyed red 182A at base.
*Stalk cavity.*—Depth 1.2 cm; width 3.5 cm.
*Lenticels.*—Present; round, diameter 1 mm; density 5 per cm2; yellow white 158A.
*Bloom of skin.*—Weak.
*Greasiness of skin.*—Slight.
*Ground color of skin.*—Yellow 12B.
*Over color of skin.*—Red 46A.
*Pattern of overcolor.*—Stripe or blush pattern.
*Amount of over color.*—Very high, 95%–100%.
*Flesh.*—Texture medium firm, crisp; juicy yellow 2D.
*Seeds.*—Quantity 9 per fruit; length 9 mm, width 5 mm; teardrop shape; greyed orange 175C.
*Market use.*—Fresh.
*Storageability.*—As for Fuji.
*Resistance to known diseases.*—None noted.

It is claimed:

1. We claim a new and distinct apple tree substantially as shown and described herein.

* * * * *

UNITED STATES PATENT AND TRADEMARK OFFICE

CERTIFICATE OF CORRECTION

PATENT NO. : PP 18,661 P2
APPLICATION NO. : 11/400782
DATED : March 25, 2008
INVENTOR(S) : David Austin It is certified that error appears in the above-identified patent and that said Letters Patent is hereby corrected as shown below:

Column 2,

Line 5, “group of plants, the new variety” should read -- group of plants, of the new variety--; and Line 13, “20 mm” should read -- 20 cm--.

Signed and Sealed this

Twenty-fourth Day of June, 2008

JON W. DUDAS
*Director of the United States Patent and Trademark Office*